United States Patent
Sánchez Vives et al.

(10) Patent No.: US 10,762,988 B2
(45) Date of Patent: Sep. 1, 2020

(54) MOTOR TRAINING

(71) Applicants: UNIVERSITAT DE BARCELONA, Barcelona (ES); INSTITUCIÓ CATALANA DE RECERCA I ESTUDIS AVANÇATS, Barcelona (ES); INSTITUT D'INVESTIGACIONS BIOMÈDIQUES AUGUST PI I SUNYER (IDIBAPS), Barcelona (ES)

(72) Inventors: Mavi Sánchez Vives, Barcelona (ES); Mel Slater, Barcelona (ES)

(73) Assignees: UNIVERSITAT DE BARCELONA, Barelona (ES); INSTITUT D'INVESTIGACIONS BIOMÈDIQUES AUGUST PI I SUNYER (IDIBAPS), Barcelona (ES); INSTITUCIÓ CATALANA DE RECERCA I ESTUDIS AVANÇATS, Barcelona (ES)

( * ) Notice: Subject to any disclaimer, the term of this patent is extended or adjusted under 35 U.S.C. 154(b) by 403 days.

(21) Appl. No.: 15/883,677

(22) Filed: Jan. 30, 2018

(65) Prior Publication Data
US 2018/0151258 A1    May 31, 2018

Related U.S. Application Data

(63) Continuation of application No. PCT/EP2016/068201, filed on Jul. 29, 2016.

(30) Foreign Application Priority Data

Jul. 31, 2015 (EP) .................................... 15382406

(51) Int. Cl.
*G16H 20/30* (2018.01)
*G06F 19/00* (2018.01)
(Continued)

(52) U.S. Cl.
CPC ......... *G16H 20/30* (2018.01); *A63B 24/0075* (2013.01); *G06F 3/012* (2013.01);
(Continued)

(58) Field of Classification Search
CPC ...................................................... G16H 20/30
See application file for complete search history.

(56) References Cited

U.S. PATENT DOCUMENTS

2007/0179558 A1*  8/2007  Gliner ................ A61N 1/36082
                                                            607/45
2011/0230792 A1    9/2011  Sarig-Bahat
(Continued)

FOREIGN PATENT DOCUMENTS

WO    2014186739 A1    11/2014
WO    2015044851 A2    4/2015

OTHER PUBLICATIONS

International Search Report in corresponding PCT Application No. PCT/EP2016/068201, dated Nov. 16, 2016.
(Continued)

*Primary Examiner* — James S. McClellan

(57) ABSTRACT

A method for motor training comprising: receiving from one or more sensors an orientation of a head mounted display of the subject; adapting a base video signal representing an avatar of the subject in a virtual reality to be displayed on the head mounted display wherein the avatar comprises a virtual limb corresponding to the limb that is injured; and sending the base video signal to the head mounted display for visualization. The method further comprises in response to a trigger signal from the subject, sending an exercise video signal representing the avatar in the virtual reality performing an exercise to start the visual rendering of the exercise in the head mounted display, even though the corresponding real limb is substantially immobile and provides no input at all. Such exercise is aimed at rehabilitation of the limb from
(Continued)

the injury with the virtual limb corresponding to the immobile limb and it is displayed taking into account the orientation of the head mounted display. A computer program and computing systems for providing a treatment session for motor training are also disclosed.

17 Claims, 2 Drawing Sheets

(51) Int. Cl.
| | |
|---|---|
| A63B 24/00 | (2006.01) |
| G06F 3/01 | (2006.01) |
| G09B 5/06 | (2006.01) |
| G09B 19/00 | (2006.01) |
| G16H 30/40 | (2018.01) |
| G06F 3/023 | (2006.01) |
| G06F 3/033 | (2013.01) |
| H04R 1/10 | (2006.01) |

(52) U.S. Cl.
CPC .......... *G06F 3/016* (2013.01); *G06F 19/3481* (2013.01); *G09B 5/065* (2013.01); *G09B 19/003* (2013.01); *A63B 2220/803* (2013.01); *A63B 2220/806* (2013.01); *A63B 2220/836* (2013.01); *G06F 3/015* (2013.01); *G06F 3/023* (2013.01); *G06F 3/0334* (2013.01); *G16H 30/40* (2018.01); *H04R 1/10* (2013.01)

(56) References Cited

U.S. PATENT DOCUMENTS

| | | |
|---|---|---|
| 2014/0287389 A1 | 9/2014 | Kallmann et al. |
| 2015/0054850 A1 | 2/2015 | Tanaka |
| 2015/0138065 A1* | 5/2015 | Alfieri .................... G06F 3/011 345/156 |

OTHER PUBLICATIONS

Giraux et al., Illusory Movements of the Paralyzed Limb Restore Motor Cortex Activity, Academic Press, NeuroImage 20 (2003), pp. S107-S111.

Perez-Marcos et al., Inducing a Virtual Hand Ownership Illusion Through a Brain-Computer Interface, Sensory and Motor Systems, NeuroReport 2009, vol. 20 No. 6, pp. 589-594, DOI: 10.1097/WNR.0b013e32832a0a2a.

* cited by examiner

MOTOR TRAINING

CROSS-REFERENCE TO RELATED APPLICATIONS

This application relates to and claims the benefit and priority to International Application No. PCT/EP2016/068201, filed Jul. 29, 2016, claims the benefit and priority to European Patent Application 15 382 406.5, filed Jul. 31, 2015.

TECHNICAL FIELD

The present disclosure relates to methods, systems and computer readable media for motor training of a subject, and in particular of a limb of a subject.

BACKGROUND

Motor training, and in particular rehabilitation and physical therapy are optimal when assessment, monitoring, adherence to the therapy program and patient engagement can be achieved.

Different processes are generally involved in physical therapy, namely physical examination, evaluation, assessment, therapy intervention, monitoring, and modification of the therapy program according to patient recovery. In traditional physical therapy, after a preliminary step of diagnostic and quantitative measurements, a patient is guided by a trained therapist to perform specific therapeutic exercises correctly. The tasks performed are designed according to the recovery plan and imply repetitions where the therapist needs to evaluate the exercise both qualitatively and quantitatively.

With recent technological advances developed in Virtual Reality (VR), innovative approaches to improve traditional physical therapy and rehabilitation practice can be explored. Typically, virtual reality is used in such therapies with a screen placed in front of a patient. On the screen, the patient's own movements are visualized. The VR is thus used in combination with actual physical therapy. The visual feedback motivates the patient and the (VR) computer system may also keep track of all exercises completed and thus again increase the patient's motivation.

An alternative use of VR is in applying a games setting. For example, the patient is actually walking on a treadmill or cycling on a static training bike, but the VR provides a stimulating environment of a run on the beach, a ride through a forest or otherwise.

US2014287389A discloses virtual reality-based adaptive systems and methods for improving the delivery of physical therapy and rehabilitation. The invention comprises an interactive software solution for tracking, monitoring and logging user performance wherever sensor capability is present. To provide therapists with the ability to observe and analyze different motion characteristics from the exercises performed by patients, novel visualization techniques are provided for specific solutions. These visualization techniques include color-coded therapist-customized visualization features for motion analysis.

US2011230792A discloses a system and method of motion assessment for use in medical analysis and treatment of motion impairments. The system is configured to stimulate, monitor and analyze voluntary movements of a subject. A surround-display is used to stimulate movement of the subject, a motion tracker monitors the movements of the subject, and a processor receives data from the motion tracker and may be configured to control the surround-display.

Commercial software solutions are available for improving physical therapy. Exoskeletons and robotic limbs with force feedback have also been employed for assisting impaired patients. However, these involve cumbersome and costly devices.

Moreover, the above mentioned processes do neither consider nor particularly focus in cases in which the therapy applies to a partially or completely immobilized limb covered with plaster, or a stroke impaired limb without mobility at all.

In examples of the present disclosure, at least some of the aforementioned problems are at least partially resolved.

SUMMARY OF THE DISCLOSURE

According to a first aspect, a method for motor training of a substantially immobile limb of a subject is provided. The method comprises substantially continuously receiving from one or more sensors an orientation of a head mounted display of the subject, substantially continuously determining a base video signal representing an avatar of the subject in a virtual reality to be displayed on the head mounted display taking into account the orientation of the head mounted display, wherein the avatar comprises a virtual limb corresponding to the immobile limb, and sending the video base signal to the head mounted display for visualization. In accordance with this aspect, the method further comprises, in response to a trigger signal from the subject, determining an exercise video signal representing the avatar performing a physical exercise aimed at rehabilitation of the limb from the injury with the virtual limb corresponding to the immobile limb, the exercise video signal taking into account the orientation of the head mounted display, and sending the exercise video signal to the head mounted display.

A substantially "immobile" limb herein may be a limb that is completely immobile or has limited mobility and the limb may be immobile for any reason, e.g. a local lesion, due to pain, a brain lesion or imposed medical immobilisation (e.g. plaster or other) and is thus to be understood as to relate both to a limb with a reduced or deteriorated motor function and to a limb with mechanical immobilisation.

In examples according to this first aspect, a virtual treatment of an injury of a limb can result in a real physical treatment of an injured limb without the limb actually performing any or very little real physical therapy. This action takes place through the activation of cortical circuits involved in the control of the limb as well as a local action through the potential activation of micromovements following visualization of the exercises. Such a virtual treatment can reduce the actual physical rehabilitation time.

A fully immersive virtual reality may be provided. As a subject moves his/her head, the video signal reproduced on the head mounted display is adapted to the real-time orientation of the head mounted display so that it contributes to the sense of "ownership" of the virtual limb. I.e. the subject's brain is cheated via the perceptual illusion that the virtual limb belongs to the subject. In the immersive virtual reality, the subject has a virtual limb that is healthy with "normal" capabilities.

A trigger provided by the subject is necessary in order to start the virtual exercise, i.e. the display of a virtual limb performing an exercise. Because this virtual exercise is only started in response to a trigger from the subject, "agency" over the movement is achieved. This means that the subject's brain believes in fact that the subject is controlling the movement of the virtual limb. The brain thus generates the illusory perception that the real limb is performing a real exercise, rather than the virtual limb performing a virtual exercise.

Inventors have found that a virtual exercise performed by a virtual limb, can thus help motor training, and in particular a real physical rehabilitation. The virtual exercises described herein may serve to improve any motor function which has deteriorated for any reason. The deterioration of a motor function may be due to a neurological damage (i.e., stroke, spinal cord injury), traumatology injuries or old age, among other. It is however important that the virtual exercise performed actually makes sense for the subject's injury. I.e. the exercises that are performed in virtual reality should be aimed at training and/or rehabilitation of the limb from the specific injury. As it will be explained later, such exercises may range from physiotherapy exercises usually prescribed to injured individuals, to actions performed in daily life (i.e. stroke affected patients that may suffer of a complete lack of motor function, and thus are in need of regaining mobility and coordination of all conventional physiological movements, or elder people losing motor function).

The exercise to be displayed may be previously selected by e.g. a practitioner or the subject himself/herself from an exercise module comprising a plurality of pre-preprogramed physiotherapy exercises directed to rehabilitating the injured limb. A library of exercises might be established for a variety of injuries.

The goal of a motor training exercise program may be to preserve the maximum range of movement of body segments without motor function, be the lack of motor function due to internal causes (e.g. stroke) or to external causes (e.g. bone fracture). The motor training can thus even be started when actual physical exercise of the injured limb is not possible yet In some examples, the method may comprise sending a signal to a tactile feedback device. The moment of tactile feedback may be correlated to or synchronised with a virtual touch of a virtual limb during a virtual training exercise. Such a multisensory feedback, (in this case visuotactile) increases ownership stimulation in the subject, which reinforces the influence over the subject's brain plasticity and thus improves the method's results. The tactile feedback device may e.g. include one or more vibrators coupled to the injured limb.

In another aspect, a computing system comprising a memory and a processor, wherein the memory stores computer program instructions executable by the processor is disclosed. The instructions may comprise the functionality to execute a method of providing a motor training according to any of the examples disclosed herein.

In yet another aspect, a system for providing a treatment session for motor training of an injured limb of a subject with a method according to examples disclosed herein is disclosed. The system may comprise a computing system as above, a head-mounted display configured to reproduce a video signal received from the computing system, one or more sensors configured to measure an orientation of a head mounted display of the subject, and a triggering device configured to send a signal to the computing system when actuated on by the subject.

In some examples, the sensors may comprise accelerometers attached to, integrated in or coupled with the head mounted display. In other examples, the sensors may comprise cameras. Optical tracking systems with corresponding software may be used. In yet further examples, further sensors involving e.g. emitters and receivers, from which the position and orientation of the subject or the head mounted display may be derived from triangulation. In yet further examples, the sensors may include a geomagnetic field sensor integrated in the head mounted display.

In the examples disclosed herein, many different suitable head mounted displays could be used. For example, a Smartphone or tablet incorporated in a head mount may serve as the screen for the head mounted display.

In some examples, the system may further comprise headphones. The computing system in such cases may send suitable audio signals for reproduction by the headphones. Through the headphones, the subject may hear instructions about upcoming (virtual) exercises. Also audio to accompany the virtual exercises can be provided in some examples, for example when a setting for the virtual exercise is a living room or a garden or similar. The typical sounds that would be heard in such situations may be reproduced to further enhance the virtual experience.

In yet another aspect, a computer program comprising program instructions to carry out any of the methods for motor training herein explained is disclosed. The computer program product may be embodied on a computer readable medium and may comprise instructions to provoke that a controller device implements a method of providing a motor training to a subject according to examples disclosed herein.

The computer program product may be embodied on a storage medium (for example, a CD-ROM, a DVD, a USB drive, on a computer memory or on a read-only memory) or carried on a carrier signal (for example, on an electrical or optical carrier signal).

The computer program may be in the form of source code, object code, a code intermediate source and object code such as in partially compiled form, or in any other form suitable for use in the implementation of the processes. The carrier may be any entity or device capable of carrying the computer program. Further, the carrier may be a transmissible carrier such as an electrical or optical signal, which may be conveyed via electrical or optical cable or by radio or other means.

When the computer program is embodied in a signal that may be conveyed directly by a cable or other device or means, the carrier may be constituted by such cable or other device or means.

Alternatively, the carrier may be an integrated circuit in which the computer program is embedded, the integrated circuit being adapted for performing, or for use in the performance of, the relevant methods.

Additional objects, advantages and features of embodiments of the invention will become apparent to those skilled in the art upon examination of the description, or may be learned by practice of the invention.

BRIEF DESCRIPTION OF THE DRAWINGS

Non-limiting examples of the present disclosure will be described in the following, with reference to the appended drawings, in which.

DETAILED DESCRIPTION

Figure 1:
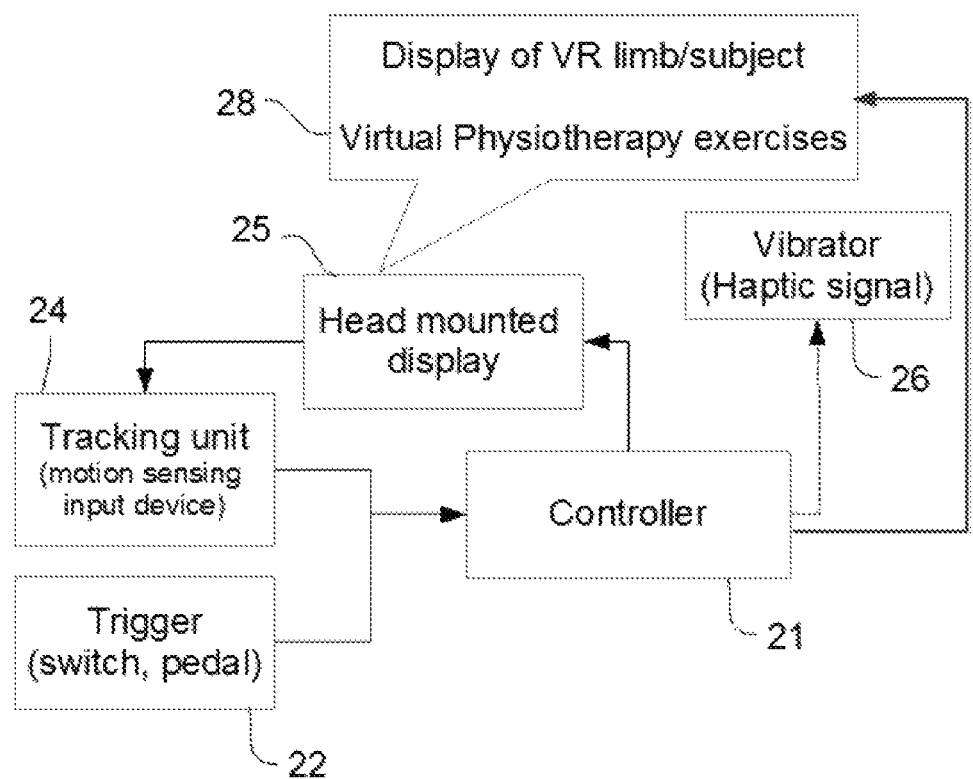
FIG. 1 illustrates a block diagram of an example of a system for providing motor training of an injured limb of a subject.

FIG. 1 illustrates a block diagram describing an example of a system for providing motor training of a substantially immobile limb (e.g. injured because of a bone fracture or with a reduced motor function) of a subject. The system comprises a computing system of controller 21 connected to a head mounted display 25, a tracking unit 24, a trigger 22 and a vibrator 26.

The head mounted display 25 (HMD) may take many suitable shapes and forms. As mentioned before, it may consist of a mobile phone or Smartphone or tablet arranged in some form of head mount. Notably, there is not necessarily a need for significant computing power in the HMD. The computing power may be provided in the actual HMD, but in some examples, the computing system may be physically separate from the HMD. The computing system in these cases may have a wireless connection with the HMD or may have a cable connection.

The tracking unit may include a plurality of sensors that in particular may be used in determining the orientation and also the position of the head mounted display. From these sensors, the point of view and direction of view of the patient may be determined and this information is used to calculate the appropriate video signal e.g. a base video signal and/or an exercise video signal, corresponding to what the patient would see in the real world. The video signal may be determined by the computing system and communicated to the head mounted display.

A base video signal may be received by the head mounted display which may represent an avatar that is not carrying out any virtual exercise, in a virtual environment. The avatar might be motionless. The video signal may further comprise an exercise video signal in which the avatar may perform a pre-programmed virtual exercise e.g. chosen by a practitioner.

The head mounted display can reproduce the received video signal e.g. base or exercise video signal, and the patient may thus see any kind of real-life situation (in different environments or settings) but in the virtual reality. A fully immersive virtual reality experience can thus be created. In a further example, a separate tracking system to track movements of the real limb may be provided, for cases where some real limb movement by the subject is possible.

The sense of embodiment may be defined as consisting of three subcomponents: the sense of self-location, the sense of agency, and the sense of body ownership. Embodiment is an important element for the system to achieve good rehabilitation results, because it basically means that the brain is deceived by the virtual reality environment, i.e., it believes that the virtual limb corresponding to the limb that is injured is the real limb, and responds to the virtually performed exercises by reactivating sensorimotor circuits associated to the moved (virtual) limb and by stimulating neurocognitive connections to the real limb so that the overall limb performance may be improved. Furthermore, micromovements in the local muscles of the injured limb may accompany the visualization of virtual exercises of that limb.

Various kinds of sensors and combinations of sensors can be used. E.g. cameras can be used to determine the orientation of the head mounted display, and can also determine movements of e.g. a non-injured limb so that these movements can also be included in the video signal.

Such cameras may be combined for example with accelerometers integrated in the head mounted display and/or accelerometers attached to the patient.

The trigger 22 may comprise a switch, a pedal, or a brain-computer interface. In an example, a foot pedal may be used for patients suffering from an arm injury. With the foot pedal, a trigger can be given. In response to the trigger, an exercise video signal, wherein a virtual exercise is carried out by the virtual limb corresponding to the injured real limb (the real limb can be completely or partially immobile) can be sent to the HMD. Prior to the trigger 22, the subject would have perceived a real-time correspondence between the images of the base video signal displayed on the HMD taking into account his/her body's actual orientation in the virtual environment. Consequently, his/her brain is led to assume the virtual body as his/her own. Once the trigger is fired, the exercise video signal may be sent to the HMD where it may be displayed. Thus, the subject may see the virtual limb carrying out a predefined exercise which may have been previously selected by e.g. a practitioner. This control of the virtual movement can induce illusory "agency" over the movement contributing to the patient's brain being cheated into thinking that the patient is actually performing the real physical exercise.

Such a foot pedal could also be used when one leg is immobile or immobilised. Alternative solutions include a hand operated switch. Any suitable trigger device that can be actuated on by a non-injured limb could potentially be used.

An alternative trigger may be in the form of a brain computer interface (BCI) or brain-machine interface (BMI). A BCI is a direct communication pathway between the brain and an external device and its application is usually directed at assisting, augmenting, or repairing human cognitive or sensory-motor functions. Brain-computer interfaces (BCI) support communication with external objects using different brain signals, for example, slow cortical potentials, event-related desynchronization, or P300, among others. A BCI enables signals from the brain to direct some external activity, such as control of a cursor or a prosthetic limb. In this example, the BCI may enable signals from the brain to send a trigger signal to the controller 21. An example of a BCI is described in "Inducing a virtual hand ownership illusion through a brain-computer interface". Neuroreport, 20(6), 589-594, by Perez-Marcos, D., Slater, M., & Sanchez-Vives, M. V.

Moreover, in some examples, a multisensory feedback may be provided. Said multisensory feedback signal may comprise a tactile feedback provided by a vibrator 26 in synchronization with the video signal of a 3D body representation display. The vibrator may be connected by cable or wirelessly with the controller. The controller may thus generate at a suitable moment a signal to activate the vibrator. More than one vibrator could be used. As mentioned above, when a vibration occurs in concurrence with a virtual limb touching an object, e.g. during a virtual limb movement, the sense of ownership of the subject regarding the virtual body is enhanced. The same sort of tactile feedback may be given when something in the virtual reality touches on the virtual limb.

The brain updates its body representation continually as a function of current multisensory input. Hence when in virtual reality multisensory data provides evidence in favour of the virtual body being the subject's body then the brain generates the perceptual illusion that this is the case, since it is the simplest hypothesis for the brain to adopt. For example, in the whole life of a person whenever they have looked towards their body, they have seen their body. In virtual reality when they look towards their body the virtual body that they see will perceptually be taken as their body.

There are a variety of ways in which such vibrating devices or alternative feedback devices may be used. In an example, if the virtual exercise comprises touching or grabbing a virtual object in the virtual reality, at the moment the injured virtual limb touches the object, a tactile feedback may be created.

Another example of the use of such tactile feedback devices may be in an introductory phase, before an actual exercise. In order to increase ownership of the virtual body, the injured limb or non-injured limb may be stimulated by such a feedback device when the video signal reproduced shows one of the virtual limbs touching a virtual object.

A further example to induce agency is for the subject to perform an exercise or straightforward movement with his/her healthy limb. If this movement is reproduced in the video signal displayed by the head mounted display, this will help cheating the subject's brain into thinking that the avatar's body corresponds to a subject's own body. If afterwards the virtual limb corresponding to the immobile limb performs a movement, this is more likely to generate illusory agency.

In some examples, headphones may be provided. The headphones may again be connected to the controller (either wireless or otherwise). Through the headphones, a patient may receive an explanation of the virtual exercise to be carried out with the appropriate instructions of when and how to activate the trigger. Also, in some examples audio feedback may be given to a patient during a virtual exercise. E.g. if a patient touches an object or reaches an object in a virtual exercise, sounds may be sent to the headphones.

The headphones may also be used for sending instructions to a patient explaining the exercises to be performed.

Motor imagery and action observation have been proposed as adjunct treatments to conventional physiotherapy. Studies have indicated that motor imagery may result in the same plastic changes in the motor system as actual physical practice. Motor imagery is the mental execution of a movement without any overt movement or without any peripheral (muscle) activation. Action observation is the observation of the action performed by others, or by oneself for example by means of mirrors of the healthy limb. It has been found that motor imagery leads to the activation of the same brain areas as actual movement and the action observation activates the mirror system. The observation of the execution of the movements by the "owned virtual body" provides contains both the components of action observation and motor imagery, but instead of being based on imagination is based in the actual visualization of the movement.

Figure 2:
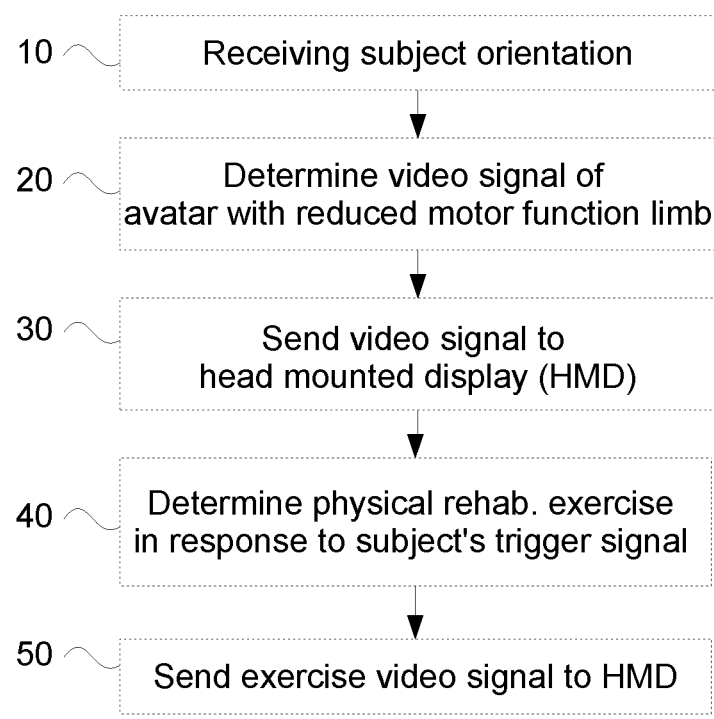
FIG. 2 illustrates a flow diagram of an example of a method for motor training of an injured limb of a subject.

Referring to FIG. 2, a flow diagram describing an example of a method for motor training of an injured limb of a subject is depicted, including the various steps of the method as processed by the controller.

At block 10, the controller may receive a subject's head orientation. As mentioned above, the subject's head orientation is measured by one or more sensors comprised in a motion sensing input device 24 which may in some examples be located on a head mounted display 25. Apart from the orientation of the HMD, also its position may be monitored and the position may be taken into account for later adapting a base video signal. For example, if a subject moves his/her head forward or rearward the base video signal to be reproduced would be changed accordingly.

At block 20, the controller may adapt a base video signal which represents an avatar of the subject, i.e. a virtual graphical representation spatially coincident with the real position of the subject undergoing the motor training. The avatar may comprise a virtual limb corresponding to the one that is injured, which will perform the motor training exercises, disregarding of the lack of motor function of the real injured limb, that is, the injured limb at the subject's body. The video signal may take into account the orientation of the head mounted display, i.e., the signal received at block 10, so that when displayed, it can induce a sense of ownership in the subject, which is particularly significant to increase the method's efficiency.

At block 30, the base video signal may be sent to the head mounted display to be visualized. As the subject perceives a real-time correspondence between the images seen on the display and his/her body's actual orientation in the environment, his/her brain is led to assume the virtual body as his/her own, that is, to experience a sense of ownership.

Thereafter, at block 40, the subject may fire a trigger signal by actuation of a sensor 22, namely a pedal, switch or BCI. Other possible trigger signals include a spoken word, e.g. "start", or simple head nodding. In response to the trigger signal, at block 50, an exercise video signal representing the avatar performing a physical rehabilitation exercise with the virtual limb corresponding to the immobile limb may be sent to the HMD where it may be displayed. The subject may thus see the avatar performing a physical rehabilitation exercise with a virtual injured limb corresponding to the real injured limb which is not moving. The exercise video signal may also be adapted to the received subject head position and/or movement.

The effects of such a trigger-response mechanism on the subject are mainly two:

The virtual body performs a movement that the real body is not performing, i.e., the virtual limb corresponding to the limb that is injured performs exercises whereas the real injured limb is impaired, which induces brain plasticity on the subject, or it is performing a movement that is amplified with respect to the one performed by the actual limb of the patient.

The subject experiences a control over the movement triggering the response signal, which induces the sense of agency or sense of control on the subject.

At this point, the subject actually may see/experience that the avatar spatially coincident with the real position (as if looking at himself/herself) moves in response to his/her action, and thus the sense of agency is stimulated on the subject. The sense of agency, or sense of control, is the subjective awareness of the subject that he/she is initiating, executing, and controlling the avatar's actions in the virtual environment, namely that he/she is the one executing the body movements.

Once the sense of agency has been established, the subject is ready to follow a motor training program, thus optimising the rehabilitation results over the injured limb.

Herein reference has been made to a base video signal and an exercise video signal.

A base video signal may represent a motionless avatar in a virtual environment. Such avatar may comprise a virtual limb which corresponds to the real injured limb of the subject which may be incapable of moving.

On the other hand, an exercise video signal may comprise a pre-programmed movement i.e. a typically prescribed physiotherapy exercise related to the subject injury, which may be chosen by a practitioner before the patient fires the trigger signal. Such exercise video signal may be part of an exercise module or library of predefined exercises. That is, the exercises performed by the virtual limb have already been pre-programmed before the trigger is fired by the subject. The exercise video signal may just be adapted to user head movement when they are displaced in the HMD.

Advantageously, the subject may follow a motor rehabilitation program for an impaired limb and experience mobility and neurocognitive improvements even though the limb is not physically performing the exercises. The rehabilitation may thus occur even during periods when active physical rehabilitation is not possible.

Not only is the proposed system more cost-effective than conventional alternatives, which may include costly externals structures and/or the medium/long term individual assistance of physicians, but the early application of therapy increases effectiveness and reduces further losses related to the injury due to inactivity. For example, in the case of patient having a leg or arm in plaster, therapy would conventionally start only after the plaster having been removed. In the meanwhile, the immobilised limb loses muscle mass and cognitive-motor capabilities. The proposed method may be applied to a plastered limb resulting in a better condition of the limb after the plaster is removed.

An example of a motor training program may contain a series of modules which are coordinated with each other. The effects that may be obtained with the virtual therapy are improved when the exercises carried out in the virtual world are the same or similar to real physical exercises that would be part of a physical rehabilitation program for curing the specific injury.

The modules may be worked out in an increasing difficulty order, thus keeping a relationship between the difficulty of each module and the injured limb improvement during the length of treatment.

For example, a series of modules might comprise, in a first instance, an initial module including joint analytical work movements, where the subject can preview a clear description of the various movements that are going to be worked through. The subject may first listen to the exercises description, then he/she may mentally pre-plan (i.e. imagine) himself/herself performing every move, which may introduce cognitive aspects in the process encompassing motor learning.

Afterwards, different kinds of motor exercises are worked out in each of the several following modules. For instance, in the case of an upper limb rehabilitation, i.e. an arm, said exercises may comprise, at the beginning and simplest level, a wrist deflection and extension, wrist rotations, hand opening and closing, deflection of the elbow extension, forearm pronation and supination. Subsequent and more complex levels may comprise exercising mobility and functionality of fingers and hand. Further modules may comprise working on executive functions, e.g. visuospatial memory and attention, as well as hand-eye coordination. More ecologically valid exercises, such as those actions performed in daily actions such as kitchen, home, etc. can also be trained while in the virtual environment.

The main goals of such motor exercises may be summarised as follows:

Preserve the maximum range of movement of body segments without mobility, either due to internal causes (e.g. stroke) or to external causes (e.g. bone fracture).

Promote the conservation of degrees of motion providing cognitive-motor training of the various joint movements.

Stimulate proprioceptive receptors as a result of the motor exercises displayed by the virtual reality system.

Provide information to activate afferent neuro-muscular movements' circuit viewing in person, thanks to the effect of possessing the body or sense of ownership.

Reduce the adaptive plastic changes in the brain that appear when limb motor function is lost.

Reactivate the brain circuits involved in the realization and sensation of specific movements.

Working hand-eye coordination (eye-hand).

Re-learn movement patterns working shifts in different directions.

Keep active neuro-muscular circuit (top-down) to preserve as much muscle tone as possible.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

What is claimed is:

1. A method for motor training of a motional impaired limb of a subject, the method comprising:
   receiving from one or more sensors an orientation of a head mounted device of the subject;
   producing a base video signal representing an avatar of the subject in a virtual reality to be exhibited on a video display of the head mounted device taking into account the orientation of the head mounted device, wherein the avatar comprises a virtual limb corresponding to the motional impaired limb of the subject;
   sending the base video signal to the head mounted device to produce on the video display of the head mounted device the avatar of the subject in the virtual reality; and
   in response to a trigger signal from the subject for the purpose of achieving in the subject agency over the motional impaired limb, sending to the head mounted device a pre-programmed exercise video signal representing the avatar in the virtual reality performing a moving exercise of the virtual limb aimed at rehabilitation of the motional impaired limb of the subject without there being any movement of the motional impaired limb, the exercise video signal taking into account the orientation of the head mounted display.

2. The method according to claim 1, wherein the method further comprises sending a signal to a tactile feedback device at a moment the virtual limb touches an object in the virtual reality.

3. The method according to claim 1, further comprising generating an audio signal describing the exercise to be performed by the virtual limb, and sending the audio signal to a device configured to reproduce the audio signal.

4. The method according to claim 1, wherein the moving exercise aimed at rehabilitation of the motional impaired limb is one or more of a joint moving exercise and a movement of the motional impaired limb as a whole.

5. The method according to claim 1, further comprising substantially continuously receiving from one or more sensors movements carried out by a non-injured limb of the subject, and substantially continuously producing a base video signal representing the avatar of the subject in the virtual reality to be exhibited on the video display of the head mounted device taking into account the orientation of the head mounted display and the movements of the non-injured limb.

6. The method according to claim 1, wherein:
   the receiving from one or more sensors an orientation of the head mounted device of the subject occurs substantially continuously; and
   the producing the base video signal occurs substantially continuously.

7. A computing system comprising a memory and a processor, wherein the memory stores computer program instructions executable by the processor, said instructions comprising functionality to execute a method of providing a motor training, the method comprising:

receiving from one or more sensors an orientation of a head mounted device of a subject;

producing a base video signal representing an avatar of the subject in a virtual reality to be exhibited on a video display of the head mounted device taking into account the orientation of the head mounted device, wherein the avatar comprises a virtual limb corresponding to a motional impaired limb of the subject;

sending the base video signal to the head mounted device to produce on the video display of the head mounted device the avatar of the subject in the virtual reality; and in response to a trigger signal from the subject for the purpose of achieving in the subject agency over the motional impaired limb, sending to the head mounted device a pre-programmed exercise video signal representing the avatar in the virtual reality performing a moving exercise of the virtual limb aimed at rehabilitation of the motional impaired limb of the subject without there being any movement of the motional impaired limb, the exercise video signal taking into account the orientation of the head mounted display.

8. A system for providing a treatment session for motor training of a motional impaired limb of a subject, the system comprising a computing system including a memory and a processor;
a head mounted device having a video display and, the head mounted device configured to receive a video signal from the computing system to produce images on the video display corresponding to the video signal;
one or more sensors configured to measure an orientation of the head mounted device; and
a triggering device configured to send a trigger signal to the computing system when acted on by the subject,
wherein the memory stores computer program instructions executable by the processor, the instructions comprising functionality to execute a method of providing a motor training, the method comprising:
receiving from the one or more sensors the orientation of a head mounted device of a subject;
producing a base video signal representing an avatar of the subject in a virtual reality to be exhibited on the video display of the head mounted device taking into account the orientation of the head mounted device, wherein the avatar comprises a virtual limb corresponding to a motional impaired limb of the subject;

sending the base video signal to the head mounted device to produce on the video display of the head mounted device the avatar of the subject in the virtual reality; and in response to a trigger signal from the subject for the purpose of achieving in the subject agency over the motional impaired limb, sending to the head mounted device a pre-programmed exercise video signal representing the avatar in the virtual reality performing a moving exercise of the virtual limb aimed at rehabilitation of the motional impaired limb of the subject without there being any movement of the motional impaired limb, the exercise video signal taking into account the orientation of the head mounted display.

9. The system according to claim 8, wherein the system further comprises headphones configured to reproduce an audio signal received from the computing system.

10. The system according to claim 8, wherein the one or more sensors configured to measure the orientation of the head mounted display comprise accelerometers attached to the head mounted display.

11. The system according to claim 8, wherein the system further comprises a tactile feedback device for providing a tactile feedback to the subject in response to a signal received from the computing system.

12. The system according to claim 11, wherein the feedback device is a vibrator configured to be attached to the subject.

13. The system according to claim 8, wherein the triggering device is a pedal.

14. The system according to claim 8, wherein the one or more sensors configured to measure the orientation of the head mounted display comprise video cameras.

15. The system according to claim 8, wherein the triggering device is a brain-computer interface.

16. The system according to claim 8, wherein the triggering device is a switch.

17. The system according to claim 8, wherein:
the receiving from one or more sensors an orientation of the head mounted device of the subject occurs substantially continuously; and
the producing the base video signal occurs substantially continuously.

* * * * *